(12) United States Patent
Koos et al.

(10) Patent No.: US 11,090,332 B2
(45) Date of Patent: Aug. 17, 2021

(54) ANTIGEN SPECIFIC MRNA CELLULAR CANCER VACCINES

(71) Applicant: Regen Biopharma, Inc, La Mesa, CA (US)

(72) Inventors: David Koos, La Mesa, CA (US); Thomas Ichim, San Diego, CA (US)

(73) Assignee: Regen Biopharma, Inc., La Mesa, CA (US)

( * ) Notice: Subject to any disclaimer, the term of this patent is extended or adjusted under 35 U.S.C. 154(b) by 0 days.

(21) Appl. No.: 15/162,370

(22) Filed: May 23, 2016

(65) Prior Publication Data

US 2017/0246207 A1    Aug. 31, 2017

Related U.S. Application Data

(60) Provisional application No. 62/165,116, filed on May 21, 2015.

(51) Int. Cl.
*A61K 35/15* (2015.01)
*A61K 38/10* (2006.01)
*A61K 38/16* (2006.01)

(52) U.S. Cl.
CPC ............. *A61K 35/15* (2013.01); *A61K 38/10* (2013.01); *A61K 38/16* (2013.01)

(58) Field of Classification Search
None
See application file for complete search history.

(56) References Cited

U.S. PATENT DOCUMENTS

| | | | |
|---|---|---|---|
| 8,263,066 B2 * | 9/2012 | Nair | A61K 39/0011 424/93.1 |
| 2008/0206270 A1 * | 8/2008 | Minev | C07K 14/4748 424/192.1 |
| 2011/0143397 A1 * | 6/2011 | Kariko | A61K 48/0041 435/70.3 |
| 2015/0086612 A1 * | 3/2015 | Sahin | A61K 39/0011 424/450 |

* cited by examiner

*Primary Examiner* — Michael D Burkhart
(74) *Attorney, Agent, or Firm* — Baumgartner Patent Law; Marc Baumgartner

(57) ABSTRACT

Disclosed are antigen specific cancer vaccines in which immunogenic epitopes are produced intracellularly by administration of modified mRNA encoding said immunogenic epitopes. In one embodiment of the invention, said modified mRNA encodes peptides derived from the protein survivin. By directly inducing gene expression of the antigens to which an immune response is desired, immunogenic peptides are generated intracellularly, thus allowing for a wider repertoire of epitopes to be presented to the adaptive immune system, which augments likelihood of successful induction of immunity.

13 Claims, No Drawings
Specification includes a Sequence Listing.

```
SEQUENCE LISTING

<160> NUMBER OF SEQ ID NOS: 8

<210> SEQ ID NO 1
<211> LENGTH: 9
<212> TYPE: PRT
<213> ORGANISM: Unknown
<220> FEATURE:
<223> OTHER INFORMATION: Description of Unknown:
      Survivin peptide

<400> SEQUENCE: 1

Ser Thr Phe Lys Asn Trp Pro Phe Leu
1               5

<210> SEQ ID NO 2
<211> LENGTH: 19
<212> TYPE: PRT
<213> ORGANISM: Unknown
<220> FEATURE:
<223> OTHER INFORMATION: Description of Unknown:
      Survivin peptide

<400> SEQUENCE: 2

Ser Thr Phe Lys Asn Trp Pro Phe Met Arg Tyr Met Ile Leu Gly Leu
1               5                   10                  15

Leu Ala Leu

<210> SEQ ID NO 3
<211> LENGTH: 14
<212> TYPE: PRT
<213> ORGANISM: Unknown
<220> FEATURE:
<223> OTHER INFORMATION: Description of Unknown:
      Survivin peptide

<400> SEQUENCE: 3

Thr Thr Ala Leu Ser Ser Thr Phe Lys Asn Trp Pro Phe Leu
1               5                   10

<210> SEQ ID NO 4
<211> LENGTH: 16
<212> TYPE: PRT
<213> ORGANISM: Unknown
<220> FEATURE:
<223> OTHER INFORMATION: Description of Unknown:
      Survivin peptide

<400> SEQUENCE: 4
```

```
Met Ala Ser Thr Phe Lys Asn Trp Pro Phe Ala Ala Ala Ala Ala Gly
1               5                   10                  15
```

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
uuauaaugac uggauguuc                                              19

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
gucuggugua ugaaggguu                                              19

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
cuccuauuuu gguuuaugc                                              19

<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gcagcgucuu ucagugcuu                                              19

ANTIGEN SPECIFIC MRNA CELLULAR CANCER VACCINES

CROSS-REFERENCE TO RELATED APPLICATIONS

This application is a non-provisional of and claims priority back to U.S. Provisional Application No. 62/165,116 filed May 21, 2015, which is hereby incorporated by reference in its entirety.

FIELD OF THE INVENTION

The invention pertains to the field of cancer immunotherapy, more particularly the invention relates to stimulation of immunity through the induction of gene expression for tumor antigens and tumor antigen derived epitopes utilizing chemically generated mRNA

DESCRIPTION OF THE INVENTION

The invention provides means of generating cellular therapies for cancer through the administration of mRNA that is chemically modified to allow for in vitro entry into cells. Particularly the invention teaches that mRNA encoding the survivin peptides a) STFKNWPFL (SEQ ID NO: 1); b) STFKNWPFMRYMILGLLAL (SEQ ID NO: 2); c) TTALSSTFKNWPFL (SEQ ID NO: 3); d) MASTFKNWPFAAAAAG (SEQ ID NO: 4) may be administered to dendritic cells, said dendritic cells being useful as a stimulator of anticancer immunity.

When practicing present invention it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To allow for the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

"Antigen-presenting cells" or "APCs" are used to refer to autologous cells that express MHC Class I and/or Class II molecules that present antigens to T cells. Examples of antigen-presenting cells include, e.g., professional or non-professional antigen processing and presenting cells. Examples of professional APCs include, e.g., B cells, whole spleen cells, monocytes, macrophages, dendritic cells, fibroblasts or non-fractionated peripheral blood mononuclear cells (PMBC). Examples of hematopoietic APCs include dendritic cells, B cells and macrophages. Of course, it is understood that one of skill in the art will recognize that other antigen-presenting cells may be useful in the invention and that the invention is not limited to the exemplary cell types described herein. APCs may be "loaded" with an antigen that is pulsed, or loaded, with antigenic peptide or recombinant peptide derived from one or more antigens. In one embodiment, a peptide is the antigen and is generally antigenic fragment capable of inducing an immune response that is characterized by the activation of helper T cells, cytolytic T lymphocytes (cytolytic T cells or CTLs) that are directed against a malignancy or infection by a mammal. In one, embodiment the peptide includes one or more peptide fragments of an antigen that are presented by class I MHC or class II MHC molecules. The skilled artisan will recognize that peptides or protein fragments that are one or more fragments of other antigens may used with the present invention and that the invention is not limited to the exemplary peptides, tumor cells, cell clones, cell lines, cell supernatants, cell membranes, and/or antigens that are described herein.

"Dendritic cell" or "DC" refer to all DCs useful in the present invention, that is, DC is various stages of differentiation, maturation and/or activation. In one embodiment of the present invention, the dendritic cells and responding T cells are derived from healthy volunteers. In another embodiment, the dendritic cells and T cells are derived from patients with cancer or other forms of tumor disease. In yet another embodiment, dendritic cells are used for either autologous or allogeneic application.

"Effective amount" refers to a quantity of an antigen or epitope that is sufficient to induce or amplify an immune response against a tumor antigen, e.g., a tumor cell.

"Vaccine" refers to compositions that affect the course of the disease by causing an effect on cells of the adaptive immune response, namely, B cells and/or T cells. The effect of vaccines can include, for example, induction of cell mediated immunity or alteration of the response of the T cell to its antigen.

"Immunologically effective" refers to an amount of antigen and antigen presenting cells loaded with one or more heat-shocked and/or killed tumor cells that elicit a change in the immune response to prevent or treat a cancer. The amount of antigen-loaded and/or antigen-loaded APCs inserted or reinserted into the patient will vary between individuals depending on many factors. For example, different doses may be required for an effective immune response in a human with a solid tumor or a metastatic tumor.

"Cancer cell antigen" refers to cells that have been stresses and killed in accordance with the present invention. Briefly, the cancer cells may be treated or stressed such that the cancer cell increases the expression of heat-shock proteins, such as HSP70, HSP60 and GP96, which are a class of proteins that are known to act as molecular chaperones for proteins that are or may be degraded. Generally, these heat-shock proteins will stabilize internal cancer cell antigens such that the cancer cells may include more highly immunogenic cancer cell-specific antigens.

"Contacted" and "exposed", when applied to an antigen and APC, are used herein to describe the process by which an antigen is placed in direct juxtaposition with the APC. To achieve antigen presentation by the APC, the antigen is provided in an amount effective to "prime" the APCs to express antigen-loaded MHC class I and/or class II antigens on the cell surface.

"Therapeutically effective amount" refers to the amount of antigen-loaded APCs that, when administered to an animal in combination, is effective to kill cancer cells within the animal. The methods and compositions of the present invention are equally suitable for killing a cancer cell or cells both in vitro and in vivo. When the cells to be killed are located within an animal, the present invention may be used in conjunction or as part of a course of treatment that may also include one or more anti-neoplastic agent, e.g., chemical, irradiation, X-rays, UV-irradiation, microwaves, electronic emissions, and the like. The skilled artisan will recognize that the present invention may be used in conjunction with therapeutically effective amount of pharmaceutical composition such a DNA damaging compound, such as, Adriamycin, 5-fluorouracil, etoposide, camptothecin, actinomycin-D, mitomycin C, cisplatin and the like. However, the present invention includes live cells that are going to activate other immune cells that may be affected by the DNA damaging agent. As such, any chemical and/or other course of treatment will generally be timed to maximize the adaptive immune response while at the same time aiding to kill as many cancer cells as possible.

"Antigen-loaded dendritic cells," "antigen-pulsed dendritic cells" and the like refer to DCs that have been contacted with an antigen, in this case, cancer cells that have been heat-shocked. Often, dendritic cells require a few hours, or up to a day, to process the antigen for presentation to naive and memory T-cells. It may be desirable to pulse the DC with antigen again after a day or two in order to enhance the uptake and processing of the antigen and/or provide one or more cytokines that will change the level of maturing of the DC. Once a DC has engulfed the antigen (e.g., pre-processed heat-shocked and/or killed cancer cells), it is termed an "antigen-primed DC". Antigen-priming can be seen in DCs by immunostaining with, e.g., an antibody to the specific cancer cells used for pulsing. An antigen-loaded or pulsed DC population may be washed, concentrated, and infused directly into the patient as a type of vaccine or treatment against the pathogen or tumor cells from which the antigen originated. Generally, antigen-loaded DC are expected to interact with naive and/or memory T-lymphocytes in vivo, thus causing them to recognize and destroy cells displaying the antigen on their surfaces. In one embodiment, the antigen-loaded DC may even interact with T cells in vitro prior to reintroduction into a patient. The skilled artisan will know how to optimize the number of antigen-loaded DC per infusion, the number and the timing of infusions. For example, it will be common to infuse a patient with 1-2 million antigen-pulsed cells per infusion, but fewer cells may also induce the desired immune response.

The antigen-loaded DCs may be co-cultured with T-lymphocytes to produce antigen-specific T-cells. As used herein, the term "antigen-specific T-cells" refers to T-cells that proliferate upon exposure to the antigen-loaded APCs of the present invention, as well as to develop the ability to attack cells having the specific antigen on their surfaces. Such T-cells, e.g., cytotoxic T-cells, lyse target cells by a number of methods, e.g., releasing toxic enzymes such as granzymes and perforin onto the surface of the target cells or by effecting the entrance of these lytic enzymes into the target cell interior. Generally, cytotoxic T-cells express CD8 on their cell surface. T-cells that express the CD4 antigen CD4, commonly known as "helper" T-cells, can also help promote specific cytotoxic activity and may also be activated by the antigen-loaded APCs of the present invention. In certain embodiments, the cancer cells, the APCs and even the T-cells can be derived from the same donor whose MNC yielded the DC, which can be the patient or an HLA—or obtained from the individual patient that is going to be treated. Alternatively, the cancer cells, the APCs and/or the T-cells can be allogeneic.

The invention provides means of inducing an anti-cancer response in a mammal, comprising the steps of initially "priming" the mammal by administering an agent that causes local accumulation of antigen presenting cells. Subsequently, a tumor antigen is administered in the local area where said agents causing accumulation of antigen presenting cells is administered. A time period is allowed to pass to allow for said antigen presenting cells to traffic to the lymph nodes. Subsequently a maturation signal, or a plurality of maturation signals are administered to enhance the ability of said antigen presenting cell to activate adaptive immunity. In some embodiments of the invention activators of adaptive immunity are concurrently given, as well as inhibitors of the tumor derived inhibitors are administered to derepress the immune system.

In one embodiment priming of the patient is achieved by administration of GM-CSF subcutaneously in the area in which antigen is to be injected. Various scenarios are known in the art for administration of GM-CSF prior to administration, or concurrently with administration of antigen. The practitioner of the invention is referred to the following publications for dosage regimens of GM-CSF and also of peptide antigens [1-12]. Subsequent to priming, the invention calls for administration of tumor antigen. Various tumor antigens may be utilized, in one preferred embodiment, lysed tumor cells from the same patient area utilized. Means for generation of lyzed tumor cells are well known in the art and described in the following references [13-19]. One example method for generation of tumor lysate involves obtaining frozen autologous samples which are placed in hanks buffered saline solution (HBSS) and gentamycin 50 pg/ml followed by homogenization by a glass homogenizer. After repeated freezing and thawing, particle-containing samples are selected and frozen in aliquots after radiation with 25 kGy. Quality assessment for sterility and endotoxin content is performed before freezing. Cell lysates are subsequently administered into the patient in a preferred manner subcutaneously at the local areas where DC priming was initiated. After 12-72 hours, the patient is subsequently administered with an agent capable of inducing maturation of DC. Agents useful for the practice of the invention, in a preferred embodiment include BCG and HMGB1 peptide. Other useful agents include: a) histone DNA; b) imiquimod; c) beta-glucan; d) hsp65; e) hsp90; f) HMGB-1; g) lipopolysaccharide; h) Pam3CSK4; i) Poly I: Poly C; j) Flagellin; k) MALP-2; l) Imidazoquinoline; m) Resiquimod; n) CpG oligonucleotides; o) zymosan; p) peptidoglycan; q) lipoteichoic acid; r) lipoprotein from gram-positive bacteria; s) lipoarabinomannan from mycobacteria; t) Polyadenylic-polyuridylic acid; u) monophosphoryl lipid A; v) single stranded RNA; w) double stranded RNA; x) 852A; y) rintatolimod; z) Gardiquimod; and aa) lipopolysaccharide peptides. The procedure is performed in a preferred embodiment with the administration of IDO silencing siRNA or shRNA containing the effector sequences a) UUAUAAUGACUGGAUGUUC (SEQ ID NO: 5); b) GUCUGGUGUAUGAAGGGUU (SEQ ID NO: 6); c) CUCCUAUUUUGGUUUAUGC SEQ ID NO: 7) and d) GCAGCGUCUUUCAGUGCUU (SEQ ID NO: 8). siRNA or shRNA may be administered through various modalities including biodegradable matrices, pressure gradients or viral transfect. In another embodiment, autologous dendritic cells are generated and IDO is silenced, prior to, concurrent with or subsequent to silencing, said dendritic cells are pulsed with tumor antigen and administered systemically.

In one embodiment, an mRNA sequence encoding for survivin associated peptides is introduced to a dendritic cell in order to cause production of survivin peptides in a manner in which said survivin peptides are presented in an immunogenic manner to a cell of the adaptive immune system, with a preferred embodiment being stimulation of T cells capable of mounting a cytotoxic T cell response. In one embodiment, mRNA encoding for peptides selected from a group comprising of:

| | | |
|---|---|---|
| a) | STFKNWPFL; | (SEQ ID NO: 1) |
| b) | STFKNWPFMRYMILGLLAL; | (SEQ ID NO: 2) |
| c) and | TTALSSTFKNWPFL; | (SEQ ID NO: 3) |
| d) | MASTFKNWPFAAAAAG. | (SEQ ID NO: 4) |

In another embodiment, administration of peptides themselves is utilized as a means of evoking an antitumor response, said peptides administered in combination with immunological adjuvants capable of augmenting type 1 immunity and reducing type 2 immunity.

Culture of dendritic cells is well known in the art, for example, U.S. Pat. No. 6,936,468, issued to Robbins, et al., for the use of tolerogenic dendritic cells for enhancing tolerogenicity in a host and methods for making the same. Although the current invention aims to reduce tolerogenesis, the essential means of dendritic cell generation are disclosed in the patent. U.S. Pat. No. 6,734,014, issued to Hwu, et al., for methods and compositions for transforming dendritic cells and activating T cells. Briefly, recombinant dendritic cells are made by transforming a stem cell and differentiating the stem cell into a dendritic cell. The resulting dendritic cell is said to be an antigen presenting cell which activates T cells against MHC class I-antigen targets. Antigens for use in dendritic cell loading are taught in, e.g., U.S. Pat. No. 6,602,709, issued to Albert, et al. This patent teaches methods for use of apoptotic cells to deliver antigen to dendritic cells for induction or tolerization of T cells. The methods and compositions are said to be useful for delivering antigens to dendritic cells that are useful for inducing antigen-specific cytotoxic T lymphocytes and T helper cells. The disclosure includes assays for evaluating the activity of cytotoxic T lymphocytes. The antigens targeted to dendritic cells are apoptotic cells that may also be modified to express non-native antigens for presentation to the dendritic cells. The dendritic cells are said to be primed by the apoptotic cells (and fragments thereof) capable of processing and presenting the processed antigen and inducing cytotoxic T lymphocyte activity or may also be used in vaccine therapies. U.S. Pat. No. 6,455,299, issued to Steinman, et al., teaches methods of use for viral vectors to deliver antigen to dendritic cells. Methods and compositions are said to be useful for delivering antigens to dendritic cells, which are then useful for inducing T antigen specific cytotoxic T lymphocytes. The disclosure provides assays for evaluating the activity of cytotoxic T lymphocytes. Antigens are provided to dendritic cells using a viral vector such as influenza virus that may be modified to express non-native antigens for presentation to the dendritic cells. The dendritic cells are infected with the vector and are said to be capable of presenting the antigen and inducing cytotoxic T lymphocyte activity or may also be used as vaccines. In the practice of the invention, it is known that dendritic cells (DC) possess unique morphology similar to neuronal dendrites and were originally identified based on their ability to stimulate the adaptive immune system. Of importance to the field of tumor immunotherapy, dendritic cells appear to be the only cell in the body capable of activating naïve T cells [20]. Accordingly, in the practice of the invention utilization of mRNA or synthetically generated survivin peptides are utilized to induce tumor immunity via T cell activation by dendritic cells. The concept of dendritic cells instructing naïve T cells to differentiate into effector or memory cells is fundamental because it places the dendritic cell as the most powerful antigen presenting cell. This implies that for immunotherapeutic purposes dendritic cells do not necessarily need to be administered at high numbers in patients. One way in which dendritic cells have been described is as sentinels of the immune system that are patrolling the body in an immature state [21, 22].

In one embodiment, utilization of molecules that are, or are similar to Damage Associated Molecular Patterns (DAMPS) are utilized ex vivo, or subsequent to in vivo administration of survivin mRNA or survivin peptide pulsed dendritic cells. Contact with said DAMPS induces the DC to migrate into the draining lymph nodes through the afferent lymphatics. During the trafficking process, DC degrade ingested proteins into peptides that bind to both MHC class I molecules and MHC class II molecules. This allows the DC to: a) perform cross presentation in that they ingest exogenous antigens but present peptides in the MHC I pathway; and b) activate both CD8 (via MHC I) and CD4 (via MHC II). Interestingly, lipid antigens are processed via different pathways and are loaded onto non-classical MHC molecules of the CD1 family [23]. The possibility of utilizing DC to stimulate immunity was made into reality in animal studies that took advantage of the ability of immature DC to potently phagocytose various antigens. If the antigens possessed DAMPs, or if DAMPs were present in the environment, the DC would mature and present the antigens, resulting in stimulation of potent T cell immunity. Accordingly, in the initial studies, immature DC were incubated with various antigens, subsequent to which a maturation signal (replicating natural DAMPs) was applied and the DC were injected into animals. Thus DC were utilized as a type of "cellular adjuvant". Indeed, it was discovered that the classical adjuvants such as Fruend's Adjuvant actually contained a high concentration of DAMPs, which resulted in the stimulation of local DC at vaccination site in vivo.

For the purpose of practicing the invention, references are made to other clinical trials utilizing dendritic cells for stimulation of tumor specific immunity. These papers that will be described are hereby incorporated by reference. One of the first clinical applications of DC was prostate cancer. In an early reported, thirty three androgen resistant metastatic prostate cancer patients where treated with DC that were pulsed with peptides from a prostate specific antigen termed PMSA. Nine partial responders were identified based on NCPC criterial, plus 50% reduction of PSA. Four of the partial responders were also responders in the phase I study, with an average response duration of 225 days. Their combined average total response period was over 370 days. Five other responders in the secondary immunizations at the Phase II were nonresponders in the phase I study. Their average partial response period was 196 days. These data support the safety of follow-up infusion of DC that have been pulsed with tumor antigen derived peptide [24].

The same group published a subsequent paper on an additional 33 patients that had not received prior DC immunization in the Phase I. All subjects received six infusions of DC pulsed with PSM-P1 and -P2 at six week intervals without any treatment associated adverse events. Six partial and two complete responders were identified in the phase II study based on NPCP criteria, plus 50% reduction of prostate-specific antigen (PSA), or resolution in previously measurable lesions on ProstaScint scan [25]. The same group analyzed immune response in patients who had clinical remission or relapsed. A strong correlation was found between delayed type hypersensitivity response to the PSM-P1 and PSM-P2 and clinical response [26].

Another subsequent study utilized DC generated using GM-CSF and IL-4 but pulsed with PAP, another prostate antigen. Specifically, the PAP was delivered to the DC by means of generation of a PAP-GM-CSF fusion protein. Two intravenous infusions of the generated cells were performed one month apart in 12 patients with androgen resistant prostate cancer. The infusions were followed by three s.c. monthly doses of the fusion protein without cells. Treatment was well tolerated and circulating prostate-specific antigen levels dropped in three patients. Immune response to the fusion protein was observed, as well as to PAP [27].

In addition to prostate cancer, in which FDA approval has been granted for the Provenge drug, numerous trials have been conducted in a wide variety of cancers. All the trials demonstrated safety, without serious adverse effects of DC administration, as well as some degree of therapeutic efficacy. Trials have been conducted in melanoma [28-79], soft tissue sarcoma [80], thyroid [81-83], glioma [17, 19, 84-103], multiple myeloma, [104-112], lymphoma [113-115], leukemia [116-123], as well as liver [124-129], lung [130-143], ovarian [144-147], and pancreatic cancer [148-150].

Within the context of the invention, dendritic cells are utilized to stimulate specific cytotoxic T cells (CTL) targeting survivin expressing tumors. It is to be understood by the practitioner of the invention that modifications survivin mRNA or survivin peptides may be made to augment generation of CTL that are capable of killing survivin expressing tumors. CTL play an important role in eradicating tumor cells and virus-infected cells. Unlike antibodies, which bind foreign proteins in their native form, CTL recognize short fragments of intracellular antigens, 8-10 amino acids in length, complexed with MHC Class I molecules. Cytosolic peptides are transported across the endoplasmic reticulum (ER) membrane with the help of the ATP-dependent transporters associated with antigen processing (TAP). Peptides complexed with Class I molecules in the ER are then transported to the cell surface for recognition by CTL. Studies with cell lines with deficits in antigen processing, (e.g., human T2 and murine RMA-S) have confirmed that TAP proteins are intimately involved in peptide transport. Alternatively, the translocation of processed proteins from the cytosol across the endoplasmic reticulum (ER) membrane is accomplished by endoplasmic reticulum-insertion signal sequences. As soon as the signal sequence of a growing polypeptide chain has emerged from the ribosome, it is bound by the signal recognition particle (SRP) and the complex is specifically targeted to the ER membrane by an interaction with the membrane bound SRP receptor. An additional targeting pathway is the signal sequence receptor complex, which is a major protein of the eukaryotic ER membrane. While translocation usually occurs during translation, protein precursors have also been shown to be imported into the ER after their synthesis has been completed. After translocation, peptides complexed with class I molecules in the ER are transported to the cell surface for recognition by the CTL.

In one embodiment of the invention, the administration of survivin peptides together with leukocyte lysate termed "transfer factor" are utilized to induce an antitumor immune response. For the purpose of understanding the use of transfer factor therapeutically, previous publications are provided below, which are summarized and incorporated by reference.

The concept of an immunologically acting "Transfer Factor" was originally identified by Henry Lawrence in a 1956 publication [151], in which he reported simultaneous transfer of delayed hypersensitivity to diphtheria toxin and to tuberculin in eight consecutive healthy volunteers who received extracts from washed leucocytes taken from the peripheral blood of tuberculin-positive, Schick-negative donors who were highly sensitive to purified diphtheria toxin and toxoid. The leucocyte extracts used for transfer contained no detectable antitoxin. The recipient subjects were Schick-positive (<0.001 unit antitoxin per ml. serum) and tuberculin-negative at the time of transfer. All the recipients remained Schick-positive for at least 2 weeks following transfer and in every case their serum contained less than 0.001 units antitoxin at the time when they exhibited maximal skin reactivity to toxoid. The "transfer factor" that was utilized was prepared by washing packed leukocytes isolated using the bovine fibrinogen method, and washing the leukocytes twice in recipient plasma. The washed leukocytes were subsequently lysed by 7-10 freeze-thaw cycles in the presence of DNAse with Mg++. Administration of the extract was performed intradermally and subcutaneously over the deltoid area.

Given that in those early days little was known regarding T cell specificity and MHC antigen presentation, the possibility that immunological information was transmitted by these low molecular weight transfer factors was taken seriously. Transfer factors of various sizes and charges were isolated, with some concept that different antigens elicited different types of transfer factors [152, 153]. Numerous theories were proposed to the molecular nature of transfer factor. Some evidence was that it constituted chains of antibodies that were preformed but subsequently cleaved [154]. Functionally, one of the main thoughts was that transfer factor has multiple sites of action, including effects on the thymus, on lymphocyte-monocyte and/or lymphocyte-lymphocyte interactions, as well as direct effects on cells in inflammatory sites. It is also suggested that the "specificity" of transfer factor is determined by the immunologic status of the recipient rather than by informational molecules in the dialysates [155].

Burger et al [156], used exclusion chromatography to perform characterization of transfer factor. The found that specific transferring ability of transfer factor in vivo was found to reside in the major UV-absorbing peak (Fraction III). Fraction III transferred tuberculin, *candida*, or KLH-reactivity to previously negative recipients. Fraction III from nonreactive donors was ineffective. When the fractions were tested in vitro, we found that both the mitogenic activity of whole transfer factor and the suppressive activity to mitogen activation when present in transfer factor was found in Fraction I. Fraction III contained components responsible for augmentation of PHA and PWM responses. In addition, Fraction III contained the component responsible for antigen-dependent augmentation of lymphocyte transformation. Fraction IV was suppressive to antigen-induced lymphocyte transformation.

In 1992 Kirkpatrick characterized the specific transfer factor at molecular level. The transfer factor is constituted by a group of numerous molecules, of low molecular weight, from 1.0 to 6.0 kDa. The 5 kDa fraction corresponds to the transfer factor specific to antigens. There are a number of publications about the clinical indications of the transfer factor for diverse diseases, in particular those where the cellular immune response is compromised or in those where there is a deficient regulation of the immune response. It has been demonstrated that the transfer factor increases the expression of IFN-gamma and RANTES, while decreases the expression of osteopontine. Using animal models it has been reported that transfer factor possesses activity against *M. tuberculosis*, and with a model of glioma with good therapeutic results. In the clinical setting studies have reported effects against herpes zoster, herpes simplex type I, herpetic keratitis, atopic dermatitis, osteosarcoma, tuberculosis, asthma, post-herpetic neuritis, anergic coccidioidomycosis, leishmaniasis, toxoplasmosis, mucocutaneous candidiasis, pediatric infections produced by diverse pathogen germs, sinusitis, pharyngitis, and otits media. All of these diseases were studied through protocols which main goals were to study the therapeutic effects of the transfer factor, and to establish in a systematic way diverse dosage schema and time for treatment to guide the prescription of the transfer factor [157].

Numerous descriptions exist of various conditions treated with transfer factor. The majority of protocols utilized similar production procedures, essentially lysis of leukocytes and extraction of the <10 Kda fraction.

Kirkpatrick [158], described 5 anergic patients with chronic mucocutaneous candidiasis who were treated with transfer factor from donors possessing a positive delayed type hypersensitive reactions to *Candida*. In each recipient, the delayed skin reactions of the transfer factor donors appeared in the recipients, however no recipient developed reactivities not possessed by the donor. Prior to injection of transfer factor, in vitro stimulation of the patients' lymphocytes with antigens did not result in macrophage inhibitor factor production, however, after transfer factor this response was positive. Therapy with transfer factor alone did not have therapeutic benefit, however, in 2 patients treatment with amphotericin-B followed by transfer factor has produced cutaneous remissions of 18 months. This study is interesting in that it demonstrated what appeared to be transfer of immunity from a skin reaction perspective but not immunological clearing of disease. In a similar study, Rocklin [159], described 2 patients with chronic mucocutaneous candidiasis and a defect in cellular immunity. Both patients received a single injection of dialysable transfer factor from *Candida*-positive donors in an effort to reconstitute immunologic function. The transfer of cellular hypersensitivity was successful in one of the two patients and was monitored by skin tests and MIF production; however, the effect was temporary and did not change the clinical course of the patient's infection. The other patient did not respond either immunologically or clinically to transfer factor at this time, although she did respond subsequently to repeated doses of transfer factor and amphotericin B therapy. The same report described transfer factor from tuberculin-positive donors being used successfully to eradicate an infection in a patient with progressive primary tuberculosis and an acquired defect in cellular immunity. The patient had not responded clinically or bacteriologically after 7½ months of antituberculous therapy, although the organism was shown to be sensitive in vitro to the drugs she was receiving. She received 6 doses of dialysable transfer factor over a 3-month period and during this time she responded clinically, bacteriologically and roentgenographically.

An investigation into a larger number of patients, Grob [160] described a series of cases in which 409 units of transfer factor was given to 45 patients. In their report they defined one unit of transfer factor as the cell extract originating from $1-2\times10(9)$ leukocytes. Besides local pain and occasional fever no side effects were observed. Immune conversions and beneficial clinical effects were seen in 11 and 10 patients, respectively, out of 12 patients with chronic candidiasis. Immune conversion was also observed in patients with multiple sclerosis, while the clinical effects cannot yet be judged. The series also included patients with subacute sclerosing panencephalitis, HBAg-positive disorders, various immunodeficiency diseases, malignant malanoma and miscellaneous tumours. Immune conversion occurred only occasionally and the clinical effect was either non-existent or not judgeable.

In addition to immune deficiencies and bacterial infections, transfer factor has demonstrated activity in viral infections. Given the RNA containing component of transfer factor, it may be that transfer factor induced interferon alpha production, which in turn would be responsible, in part for potential antiviral activity. Pizza et al [161], described, 33 patients with low immune response to HSV antigens and suffering from herpes ocular infections were orally treated with HSV-specific transfer factor. Their relapse index was reduced from 20.1 before treatment to 0.51 after administration, with only 6/33 patients relapsing. In another study, 20 HSV-1 patients whose disease had been treated before with other therapeutic agents (including acyclovir) were administered transfer factor and used as their own controls in terms of quantification of remissions. Transfer factor was administered subcutaneously daily for 3 to 4 days during the acute phase of the disease, and subsequently at 15-day intervals for the first 6 months; followed by a continuation of monthly injections until the termination of the study period. In 6/20 patients there was a recurrence of the disease while receiving maintenance dosages of transfer factor. These patients were again given the full initial dosage schedule and reinstated again with the maintenance dosage. The results showed an important improvement in the response to transfer factor immune modulation therapy in that a statistically significant reduction in the frequency of recurrences within a one month period was observed [162].

Supporting these observations, Meduri et al [163], reported an open clinical trial in 134 patients (71 keratitis, 29 kerato-uveitis, 34 uveitis) suffering from recurrent ocular herpetic infections. The mean duration of the treatment was 358 days. The cell-mediated immune response to the viral antigens, evaluated by the lymphocyte stimulation test and the leucocyte migration test, was significantly increased by the transfer factor treatment. The total number of relapses was decreased significantly during/after transfer factor treatment, dropping from 832 before, to 89 after treatment, whereas the cumulative relapse index dropped, during the same period, from 13.2 to 4.17.

A more recent study compared transfer factor with acyclovir in treatment of varicella herpes simplex patients. A double blind clinical trial of transfer factor compared to acyclovir was carried out in which 28 patients. Treatment was administered for seven days and the patients were subsequently submitted to daily clinical observation for an additional 14 days. An analogue visual scale was implemented in order to record pain and thereby served as the clinical parameter for scoring results. The group treated with transfer factor was found to have a more favorable clinical course, P< or =0.015. Laboratory tests to assess the immune profile of the patients were performed two days prior and 14 days after initial treatment. The results of these tests showed an increase in IFN-gamma levels, augmentation in the CD4+ cell population in the transfer factor treated group. These parameters were however insignificantly modified in patients receiving acyclovir [164].

Given the association between viruses and cancer, as well as the potent stimulation of the killer arm of the immune system by transfer factor, rationale was made to treat various malignancies with transfer factor [165]. Levin et al [166], described treatment of 18 patients with osteogenic sarcoma. Of these, 13 have had or are currently receiving injections of osteogenic sarcoma-specific dialyzable transfer factor derived from healthy donors. In three patients with very small lesions, cytotoxicity was high before amputation and decreased within 2 mo after removal of tumor. Cytotoxicity was low at time of diagnosis in all patients with large tumor masses. The cytotoxicity of the patients' lymphocytes increased after administration of tumor-specific transfer factor in all patients so treated. Patients receiving nonspecific transfer factor showed evidence of declining cell-mediated cytotoxicity. Tumor-specific transfer factor may produce an increase in cell-mediated cytotoxicity to the tumor in patients with osteogenic sarcoma. This possibility is suggested by the pain and edema that occurred in the area of the tumor in patients who had metastatic disease when therapy was started and by lymphocytic infiltrates in the tumor, as well as by the increase in cell-mediated cytotoxicity and the increase in percentage of active rosette-forming cells from subnormal to normal.

Ng et al reported a controlled study in which 6 patients with stage-IV Hodgkin's disease were given transfer factor prepared from patients with Hodgkin's disease in long remission. There was an apparent increase in cell-mediated immune responses as evidenced by a significant increase in the recipients' lymphocyte responses to phytohaemagglutinin stimulation. Three out of six patients converted to positive delayed-hypersensitivity tests [167].

In head and neck cancer a study examined 67 patients of which 40 have received immunologic transfer factor from a normal donor pool. Examination of these patients revealed that lymphocyte reactivity to nonspecific mitogrens is depressed in patients who have head and neck cancer to a much greater extent than is seen in patients with other types of tumors. Th T-lymphocyte levels increased in eight of 38 patients who received nonimmune transfer factor [168].

Krown et al [169], reported on 18 patients with advanced cancer were given subcutaneous injections of pooled dialyzable transfer factor from normal donors for periods of from 9 days to 6.5 months. Minor tumor regression was observed in only two patients. Treatment with transfer factor was associated with at least a temporary increase in delayed hypersensitivity reactions in 12 of 17 patients tested, including four patients who became responsive to 2,4-dinitrochlorobenzene. In general, in vitro tests of immune function were not changed after treatment with transfer factor except for levels of C1q, and/or C3, which were increased in 6 of 10 patients tested.\

Wagner et al [170], ran a prospective randomized double-blind study of 60 patients with invasive cervical cancer, 32 were treated with transfer factor derived from leukocytes of the patients' husbands, and 28 were treated with placebo. Within the first 2 years after radical hysterectomy, five out of 32 transfer factor-treated patients and 11 out of 28 placebo-treated patients developed recurrence of malignancy. Excluding one further patient with intercurrent death this difference is significant. Subdividing the collectives, significant differences were found in patients aged below 35 years and in patients with stage I disease. Identical immune profiles were checked in leukocyte donors prior to leukophoresis and were serially checked in patients. Antigen-specific correlations were found between donors' and recipients' reactivities but not between donors' reactivity and recipient's course of the disease.

Whyte et al [171], Reported on a patient evaluation between 1976 and 1982, 63 patients who underwent pulmonary resection, mediastinal lymph node dissection, and, when indicated by the presence of mediastinal lymph node involvement, mediastinal irradiation were randomized into two groups. Group 1 (n=28) received 1 mL of pooled transfer factor at 3-month intervals after operation; group 2 (n=35) served as controls and received saline solution. There were no statistically significant differences between the two groups with respect to age, sex, tumor histology, stage of disease, or extent of resection. One patient was lost to follow-up at 96 months; follow-up was complete in all others through July 1990. In patients receiving transfer factor, the 2-, 5-, and 10-year survival rates were 82%, 64%, and 43% respectively, whereas in controls they were 63%, 43%, and 23%. Survival in patients receiving transfer factor was consistently better than in those receiving placebo. Furthermore, survival in patients receiving transfer factor was greater at all stages of disease for both adenocarcinoma and squamous cell carcinoma. Although these long-term results were not statistically significant using survival analysis with covariates (p=0.08), they confirm our previously reported short-term findings suggesting that administration of transfer factor, either through nonspecific immune stimulation, enhancement of cell-mediated immunity, or an as yet undefined mechanism, can improve survival in patients with bronchogenic carcinoma.

Subsequent studies, even from as early as the 1970s reported that transfer factor lacks antigen specificity. For example, Dupont et al [172], reported treatment of patients with transfer factor produced by the following means: a) 450 ml of healthy donor blood was drawn; b) buffy coat leukocytes (1.6×10(9)) were collected and concentrated into 1.6 ml of packed cells; c) cells were then diluted in 4 ml saline and underwent 10 freeze-thaw cycles; d) Mg++ and DNAse was added for 30 min and incubated at 37 Celsius; e) the cell lysate was dialyzed against 500 ml of distilled water for 2 day and redialyzed again using the same procedure; f) the dialysate was lyophilized and stored at −20 Celsius, before use it was dissolved using a 0.45 micron filter. The authors reported evidence for nonspecificity in the effect of transfer factor on mixed lymphocyte culture reactivity. The data suggest that in patients with immunodeficiency disease a maturation of lymphocytes may lead to a generalized increased immune responsiveness. More profoundly, the data showed that transfer factor may induce changes in the expression of histocompatibility determinants. We observed changes in the expression of determinants capable of stimulating in the mixed lymphocyte culture reaction as well as an increase in the capacity of lymphocytes to respond. A subsequent paper also supported the concept that transfer factor may induce maturation of recipient immune cells in an antigen non-specific manner [173].

More recent studies have supported the concept that transfer factor may not act as the original notion of "transferring immunity" but as a non-specific immune modulator. One possibility is that transfer factor contains an RNA component that activates one or more of the toll like receptors. Indeed original work in the area of transfer factored seemed to demonstrate an RNAse III-sensitive activity in transfer factor [153].

REFERENCES

1. Middleton G, Silcocks P, Cox T et al. Gemcitabine and capecitabine with or without telomerase peptide vaccine GV1001 in patients with locally advanced or metastatic pancreatic cancer (TeloVac): an open-label, randomised, phase 3 trial. *The Lancet. Oncology* 15(8), 829-840 (2014).
2. Mittendorf E A, Clifton G T, Holmes J P et al. Final report of the phase I/II clinical trial of the E75 (nelipepimut-S) vaccine with booster inoculations to prevent disease recurrence in high-risk breast cancer patients. *Annals of oncology: official journal of the European Society for Medical Oncology/ESMO* 25(9), 1735-1742 (2014).
3. Rahma O E, Hamilton J M, Wojtowicz M et al. The immunological and clinical effects of mutated ras peptide vaccine in combination with IL-2, GM-CSF, or both in patients with solid tumors. *Journal of translational medicine* 12 55 (2014).
4. Clancy-Thompson E, King L K, Nunnley L D, Mullins I M, Slingluff C L, Jr., Mullins D W. Peptide vaccination in Montanide adjuvant induces and GM-CSF increases CXCR3 and cutaneous lymphocyte antigen expression by tumor antigen-specific CD8 T cells. *Cancer immunology research* 1(5), 332-339 (2013).
5. Sonpavde G, Wang M, Peterson L E et al. HLA-restricted NY-ESO-1 peptide immunotherapy for metastatic castration resistant prostate cancer. *Investigational new drugs* 32(2), 235-242 (2014).
6. Geynisman D M, Zha Y, Kunnavakkam R et al. A randomized pilot phase I study of modified carcinoembryonic antigen (CEA) peptide (CAP1-6D)/montanide/GM-CSF-vaccine in patients with pancreatic adenocarcinoma. *Journal for immunotherapy of cancer* 1 8 (2013).
7. Tarhini A A, Butterfield L H, Shuai Y, Gooding W E, Kalinski P, Kirkwood J M. Differing patterns of circulating regulatory T cells and myeloid-derived suppressor cells in metastatic melanoma patients receiving anti-CTLA4 antibody and interferon-alpha or TLR-9 agonist and GM-CSF with peptide vaccination. *Journal of immunotherapy* 35(9), 702-710 (2012).
8. Walter S, Weinschenk T, Stenzl A et al. Multipeptide immune response to cancer vaccine IMA901 after single-dose cyclophosphamide associates with longer patient survival. *Nature medicine* 18(8), 1254-1261 (2012).
9. Ohno S, Okuyama R, Aruga A, Sugiyama H, Yamamoto M. Phase I trial of Wilms' Tumor 1 (WT1) peptide vaccine with GM-CSF or CpG in patients with solid malignancy. *Anticancer research* 32(6), 2263-2269 (2012).
10. Tarhini A A, Leng S, Moschos S J et al. Safety and immunogenicity of vaccination with MART-1 (26-35, 27L), gp100 (209-217, 210M), and tyrosinase (368-376, 370D) in adjuvant with PF-3512676 and GM-CSF in metastatic melanoma. *Journal of immunotherapy* 35(4), 359-366 (2012).
11. Schaefer C, Butterfield L H, Lee S et al. Function but not phenotype of melanoma peptide-specific CD8(+) T cells correlate with survival in a multiepitope peptide vaccine trial (ECOG 1696). *International journal of cancer. Journal international du cancer* 131(4), 874-884 (2012).
12. Block M S, Suman V J, Nevala W K et al. Pilot study of granulocyte-macrophage colony-stimulating factor and interleukin-2 as immune adjuvants for a melanoma peptide vaccine. *Melanoma research* 21(5), 438-445 (2011).
13. Bapsy P P, Sharan B, Kumar C et al. Open-label, multi-center, non-randomized, single-arm study to evaluate the safety and efficacy of dendritic cell immunotherapy in patients with refractory solid malignancies, on supportive care. *Cytotherapy* 16(2), 234-244 (2014).
14. Reyes D, Salazar L, Espinoza E et al. Tumour cell lysate-loaded dendritic cell vaccine induces biochemical and memory immune response in castration-resistant prostate cancer patients. *British journal of cancer* 109(6), 1488-1497 (2013).
15. Kamigaki T, Kaneko T, Naitoh K et al. Immunotherapy of autologous tumor lysate-loaded dendritic cell vaccines by a closed-flow electroporation system for solid tumors. *Anticancer research* 33(7), 2971-2976 (2013).
16. Florcken A, Kopp J, Van Lessen A et al. Allogeneic partially HLA-matched dendritic cells pulsed with autologous tumor cell lysate as a vaccine in metastatic renal cell cancer: a clinical phase I/II study. *Human vaccines & immunotherapeutics* 9(6), 1217-1227 (2013).
17. Cho D Y, Yang W K, Lee H C et al. Adjuvant immunotherapy with whole-cell lysate dendritic cells vaccine for glioblastoma multiforme: a phase II clinical trial. *World neurosurgery* 77(5-6), 736-744 (2012).
18. Alfaro C, Perez-Gracia J L, Suarez N et al. Pilot clinical trial of type 1 dendritic cells loaded with autologous tumor lysates combined with GM-CSF, pegylated IFN, and cyclophosphamide for metastatic cancer patients. *Journal of immunology* 187(11), 6130-6142 (2011).
19. Fadul C E, Fisher J L, Hampton T H et al. Immune response in patients with newly diagnosed glioblastoma multiforme treated with intranodal autologous tumor lysate-dendritic cell vaccination after radiation chemotherapy. *Journal of immunotherapy* 34(4), 382-389 (2011).
20. Steinman R M, Cohn Z A. Identification of a novel cell type in peripheral lymphoid organs of mice. I. Morphology, quantitation, tissue distribution. *The Journal of experimental medicine* 137(5), 1142-1162 (1973).
21. Banchereau J, Steinman R M. Dendritic cells and the control of immunity. *Nature* 392(6673), 245-252 (1998).
22. Trombetta E S, Mellman I. Cell biology of antigen processing in vitro and in vivo. *Annual review of immunology* 23 975-1028 (2005).
23. Itano A A, Jenkins M K. Antigen presentation to naive CD4 T cells in the lymph node. *Nature immunology* 4(8), 733-739 (2003).
24. Tjoa B A, Simmons S J, Bowes V A et al. Evaluation of phase I/II clinical trials in prostate cancer with dendritic cells and PSMA peptides. *The Prostate* 36(1), 39-44 (1998).
25. Murphy G P, Tjoa B A, Simmons S J et al. Infusion of dendritic cells pulsed with HLA-A2-specific prostate-specific membrane antigen peptides: a phase II prostate cancer vaccine trial involving patients with hormone-refractory metastatic disease. *The Prostate* 38(1), 73-78 (1999).
26. Lodge P A, Jones L A, Bader R A, Murphy G P, Salgaller M L. Dendritic cell-based immunotherapy of prostate cancer: immune monitoring of a phase II clinical trial. *Cancer research* 60(4), 829-833 (2000).
27. Burch P A, Breen J K, Buckner J C et al. Priming tissue-specific cellular immunity in a phase I trial of autologous dendritic cells for prostate cancer. *Clinical cancer research: an official journal of the American Association for Cancer Research* 6(6), 2175-2182 (2000).
28. Nestle F O, Alijagic S, Gilliet M et al. Vaccination of melanoma patients with peptide- or tumor lysate-pulsed dendritic cells. *Nature medicine* 4(3), 328-332 (1998).
29. Chakraborty N G, Sporn J R, Tortora A F et al. Immunization with a tumor-cell-lysate-loaded autologous-antigen-presenting-cell-based vaccine in melanoma. *Cancer immunology, immunotherapy: CII* 47(1), 58-64 (1998).
30. Wang F, Bade E, Kuniyoshi C et al. Phase I trial of a MART-1 peptide vaccine with incomplete Freund's adjuvant for resected high-risk melanoma. *Clinical cancer research: an official journal of the American Association for Cancer Research* 5(10), 2756-2765 (1999).
31. Thurner B, Haendle I, Roder C et al. Vaccination with mage-3A1 peptide-pulsed mature, monocyte-derived dendritic cells expands specific cytotoxic T cells and induces regression of some metastases in advanced stage IV melanoma. *The Journal of experimental medicine* 190 (11), 1669-1678 (1999).
32. Thomas R, Chambers M, Boytar R et al. Immature human monocyte-derived dendritic cells migrate rapidly to draining lymph nodes after intradermal injection for melanoma immunotherapy. *Melanoma research* 9(5), 474-481 (1999).
33. Mackensen A, Herbst B, Chen J L et al. Phase I study in melanoma patients of a vaccine with peptide-pulsed dendritic cells generated in vitro from CD34(+) hematopoietic progenitor cells. *International journal of cancer. Journal international du cancer* 86(3), 385-392 (2000).
34. Panelli M C, Wunderlich J, Jeffries J et al. Phase 1 study in patients with metastatic melanoma of immunization with dendritic cells presenting epitopes derived from the melanoma-associated antigens MART-1 and gp100. *Journal of immunotherapy* 23(4), 487-498 (2000).
35. Schuler-Thurner B, Dieckmann D, Keikavoussi P et al. Mage-3 and influenza-matrix peptide-specific cytotoxic T cells are inducible in terminal stage HLA-A2.1+ melanoma patients by mature monocyte-derived dendritic cells. *Journal of immunology* 165(6), 3492-3496 (2000).
36. Lau R, Wang F, Jeffery G et al. Phase I trial of intravenous peptide-pulsed dendritic cells in patients with metastatic melanoma. *Journal of immunotherapy* 24(1), 66-78 (2001).
37. Banchereau J, Palucka A K, Dhodapkar M et al. Immune and clinical responses in patients with metastatic melanoma to CD34(+) progenitor-derived dendritic cell vaccine. *Cancer research* 61(17), 6451-6458 (2001).
38. Schuler-Thurner B, Schultz E S, Berger T G et al. Rapid induction of tumor-specific type 1 T helper cells in metastatic melanoma patients by vaccination with mature, cryopreserved, peptide-loaded monocyte-derived dendritic cells. *The Journal of experimental medicine* 195 (10), 1279-1288 (2002).
39. Palucka A K, Dhodapkar M V, Paczesny S et al. Single injection of CD34+ progenitor-derived dendritic cell vaccine can lead to induction of T-cell immunity in patients with stage IV melanoma. *Journal of immunotherapy* 26(5), 432-439 (2003).
40. Bedrosian I, Mick R, Xu S et al. Intranodal administration of peptide-pulsed mature dendritic cell vaccines results in superior CD8+ T-cell function in melanoma patients. *Journal of clinical oncology: official journal of the American Society of Clinical Oncology* 21(20), 3826-3835 (2003).
41. Slingluff C L, Jr., Petroni G R, Yamshchikov G V et al. Clinical and immunologic results of a randomized phase II trial of vaccination using four melanoma peptides either administered in granulocyte-macrophage colony-stimulating factor in adjuvant or pulsed on dendritic cells. *Journal of clinical oncology: official journal of the American Society of Clinical Oncology* 21(21), 4016-4026 (2003).
42. Hersey P, Menzies S W, Halliday G M et al. Phase I/II study of treatment with dendritic cell vaccines in patients with disseminated melanoma. *Cancer immunology, immunotherapy: CII* 53(2), 125-134 (2004).
43. Vilella R, Benitez D, Mila J et al. Pilot study of treatment of biochemotherapy-refractory stage IV melanoma patients with autologous dendritic cells pulsed with a heterologous melanoma cell line lysate. *Cancer immunology, immunotherapy: CII* 53(7), 651-658 (2004).
44. Palucka A K, Connolly J, Ueno H et al. Spontaneous proliferation and type 2 cytokine secretion by CD4+T cells in patients with metastatic melanoma vaccinated with antigen-pulsed dendritic cells. *Journal of clinical immunology* 25(3), 288-295 (2005).
45. Banchereau J, Ueno H, Dhodapkar M et al. Immune and clinical outcomes in patients with stage IV melanoma vaccinated with peptide-pulsed dendritic cells derived from CD34+ progenitors and activated with type I interferon. *Journal of immunotherapy* 28(5), 505-516 (2005).
46. Trakatelli M, Toungouz M, Blocklet D et al. A new dendritic cell vaccine generated with interleukin-3 and interferon-beta induces CD8+ T cell responses against NA17-A2 tumor peptide in melanoma patients. *Cancer immunology, immunotherapy: CII* 55(4), 469-474 (2006).
47. Salcedo M, Bercovici N, Taylor R et al. Vaccination of melanoma patients using dendritic cells loaded with an allogeneic tumor cell lysate. *Cancer immunology, immunotherapy: CII* 55(7), 819-829 (2006).
48. Linette G P, Zhang D, Hodi F S et al. Immunization using autologous dendritic cells pulsed with the melanoma-associated antigen gp100-derived G280-9V peptide elicits CD8+ immunity. *Clinical cancer research: an official journal of the American Association for Cancer Research* 11(21), 7692-7699 (2005).
49. Escobar A, Lopez M, Serrano A et al. Dendritic cell immunizations alone or combined with low doses of interleukin-2 induce specific immune responses in melanoma patients. *Clinical and experimental immunology* 142(3), 555-568 (2005).
50. Tuettenberg A, Becker C, Huter E, Knop J, Enk A H, Jonuleit H. Induction of strong and persistent MelanA/MART-1-specific immune responses by adjuvant dendritic cell-based vaccination of stage II melanoma patients. *International journal of cancer. Journal international du cancer* 118(10), 2617-2627 (2006).
51. Schadendorf D, Ugurel S, Schuler-Thurner B et al. Dacarbazine (DTIC) versus vaccination with autologous peptide-pulsed dendritic cells (DC) in first-line treatment of patients with metastatic melanoma: a randomized phase III trial of the DC study group of the DeCOG. *Annals of oncology: official journal of the European Society for Medical Oncology/ESMO* 17(4), 563-570 (2006).
52. Di Pucchio T, Pilla L, Capone I et al. Immunization of stage IV melanoma patients with Melan-A/MART-1 and gp100 peptides plus IFN-alpha results in the activation of specific CD8(+) T cells and monocyte/dendritic cell precursors. *Cancer research* 66(9), 4943-4951 (2006).
53. Nakai N, Asai J, Ueda E, Takenaka H, Katoh N, Kishimoto S. Vaccination of Japanese patients with advanced melanoma with peptide, tumor lysate or both peptide and tumor lysate-pulsed mature, monocyte-derived dendritic cells. *The Journal of dermatology* 33(7), 462-472 (2006).
54. Palucka A K, Ueno H, Connolly J et al. Dendritic cells loaded with killed allogeneic melanoma cells can induce objective clinical responses and MART-1 specific CD8+ T-cell immunity. *Journal of immunotherapy* 29(5), 545-557 (2006).
55. Lesimple T, Neidhard E M, Vignard V et al. Immunologic and clinical effects of injecting mature peptide-loaded dendritic cells by intralymphatic and intranodal routes in metastatic melanoma patients. *Clinical cancer research: an official journal of the American Association for Cancer Research* 12(24), 7380-7388 (2006).
56. Guo J, Zhu J, Sheng X et al. Intratumoral injection of dendritic cells in combination with local hyperthermia induces systemic antitumor effect in patients with advanced melanoma. *International journal of cancer. Journal international du cancer* 120(11), 2418-2425 (2007).
57. O'rourke M G, Johnson M K, Lanagan C M et al. Dendritic cell immunotherapy for stage IV melanoma. *Melanoma research* 17(5), 316-322 (2007).
58. Bercovici N, Haicheur N, Massicard S et al. Analysis and characterization of antitumor T-cell response after administration of dendritic cells loaded with allogeneic tumor lysate to metastatic melanoma patients. *Journal of immunotherapy* 31(1), 101-112 (2008).
59. Hersey P, Halliday G M, Farrelly M L, Desilva C, Lett M, Menzies S W. Phase I/II study of treatment with matured dendritic cells with or without low dose IL-2 in patients with disseminated melanoma. *Cancer immunology, immunotherapy: CII* 57(7), 1039-1051 (2008).
60. Von Euw E M, Barrio M M, Furman D et al. A phase I clinical study of vaccination of melanoma patients with dendritic cells loaded with allogeneic apoptotic/necrotic melanoma cells. Analysis of toxicity and immune response to the vaccine and of IL-10-1082 promoter genotype as predictor of disease progression. *Journal of translational medicine* 6 6 (2008).
61. Carrasco J, Van Pel A, Neyns B et al. Vaccination of a melanoma patient with mature dendritic cells pulsed with MAGE-3 peptides triggers the activity of nonvaccine anti-tumor cells. *Journal of immunology* 180(5), 3585-3593 (2008).
62. Redman B G, Chang A E, Whitfield J et al. Phase Ib trial assessing autologous, tumor-pulsed dendritic cells as a vaccine administered with or without IL-2 in patients with metastatic melanoma. *Journal of immunotherapy* 31(6), 591-598 (2008).
63. Daud A I, Mirza N, Lenox B et al. Phenotypic and functional analysis of dendritic cells and clinical outcome in patients with high-risk melanoma treated with adjuvant granulocyte macrophage colony-stimulating factor. *Journal of clinical oncology: official journal of the American Society of Clinical Oncology* 26(19), 3235-3241 (2008).
64. Engell-Noerregaard L, Hansen T H, Andersen M H, Thor Straten P, Svane I M. Review of clinical studies on dendritic cell-based vaccination of patients with malignant melanoma: assessment of correlation between clinical response and vaccine parameters. *Cancer immunology, immunotherapy: CII* 58(1), 1-14 (2009).
65. Nakai N, Katoh N, Germeraad W T et al. Immunohistological analysis of peptide-induced delayed-type hypersensitivity in advanced melanoma patients treated with melanoma antigen-pulsed mature monocyte-derived dendritic cell vaccination. *Journal of dermatological science* 53(1), 40-47 (2009).
66. Dillman R O, Selvan S R, Schiltz P M et al. Phase II trial of dendritic cells loaded with antigens from self-renewing, proliferating autologous tumor cells as patient-specific antitumor vaccines in patients with metastatic melanoma: final report. *Cancer biotherapy & radiopharmaceuticals* 24(3), 311-319 (2009).
67. Chang J W, Hsieh J J, Shen Y C et al. Immunotherapy with dendritic cells pulsed by autologous dactinomycin-induced melanoma apoptotic bodies for patients with malignant melanoma. *Melanoma research* 19(5), 309-315 (2009).
68. Trepiakas R, Berntsen A, Hadrup S R et al. Vaccination with autologous dendritic cells pulsed with multiple tumor antigens for treatment of patients with malignant melanoma: results from a phase I/II trial. *Cytotherapy* 12(6), 721-734 (2010).
69. Jacobs J F, Punt C J, Lesterhuis W J et al. Dendritic cell vaccination in combination with anti-CD25 monoclonal antibody treatment: a phase I/II study in metastatic melanoma patients. *Clinical cancer research: an official journal of the American Association for Cancer Research* 16(20), 5067-5078 (2010).
70. Ribas A, Camacho L H, Lee S M et al. Multicenter phase II study of matured dendritic cells pulsed with melanoma cell line lysates in patients with advanced melanoma. *Journal of translational medicine* 8 89 (2010).
71. Ridolfi L, Petrini M, Fiammenghi L et al. Unexpected high response rate to traditional therapy after dendritic cell-based vaccine in advanced melanoma: update of clinical outcome and subgroup analysis. *Clinical & developmental immunology* 2010 504979 (2010).
72. Cornforth A N, Fowler A W, Carbonell D J, Dillman R O. Resistance to the proapoptotic effects of interferon-gamma on melanoma cells used in patient-specific dendritic cell immunotherapy is associated with improved overall survival. *Cancer immunology, immunotherapy: CII* 60(1), 123-131 (2011).
73. Lesterhuis W J, Schreibelt G, Scharenborg N M et al. Wild-type and modified gp100 peptide-pulsed dendritic cell vaccination of advanced melanoma patients can lead to long-term clinical responses independent of the peptide used. *Cancer immunology, immunotherapy: CII* 60(2), 249-260 (2011).
74. Bjoern J, Brimnes M K, Andersen M H, Thor Straten P, Svane I M. Changes in peripheral blood level of regulatory T cells in patients with malignant melanoma during treatment with dendritic cell vaccination and low-dose IL-2. *Scandinavian journal of immunology* 73(3), 222-233 (2011).
75. Steele J C, Rao A, Marsden J R et al. Phase I/II trial of a dendritic cell vaccine transfected with DNA encoding melan A and gp100 for patients with metastatic melanoma. *Gene therapy* 18(6), 584-593 (2011).
76. Kim D S, Kim D H, Goo B et al. Immunotherapy of malignant melanoma with tumor lysate-pulsed autologous monocyte-derived dendritic cells. *Yonsei medical journal* 52(6), 990-998 (2011).
77. Ellebaek E, Engell-Noerregaard L, Iversen T Z et al. Metastatic melanoma patients treated with dendritic cell vaccination, Interleukin-2 and metronomic cyclophosphamide: results from a phase II trial. *Cancer immunology, immunotherapy: CII* 61(10), 1791-1804 (2012).
78. Dillman R O, Cornforth A N, Depriest C et al. Tumor stem cell antigens as consolidative active specific immunotherapy: a randomized phase II trial of dendritic cells versus tumor cells in patients with metastatic melanoma. *Journal of immunotherapy* 35(8), 641-649 (2012).
79. Dannull J, Haley NR, Archer G et al. Melanoma immunotherapy using mature DCs expressing the constitutive proteasome. *The Journal of clinical investigation* 123(7), 3135-3145 (2013).
80. Finkelstein S E, Iclozan C, Bui M M et al. Combination of external beam radiotherapy (EBRT) with intratumoral injection of dendritic cells as neo-adjuvant treatment of high-risk soft tissue sarcoma patients. *International journal of radiation oncology, biology, physics* 82(2), 924-932 (2012).
81. Stift A, Sachet M, Yagubian R et al. Dendritic cell vaccination in medullary thyroid carcinoma. *Clinical cancer research: an official journal of the American Association for Cancer Research* 10(9), 2944-2953 (2004).
82. Kuwabara K, Nishishita T, Morishita M et al. Results of a phase I clinical study using dendritic cell vaccinations for thyroid cancer. *Thyroid: official journal of the American Thyroid Association* 17(1), 53-58 (2007).
83. Bachleitner-Hofmann T, Friedl J, Hassler M et al. Pilot trial of autologous dendritic cells loaded with tumor lysate(s) from allogeneic tumor cell lines in patients with metastatic medullary thyroid carcinoma. *Oncology reports* 21(6), 1585-1592 (2009).
84. Yu J S, Wheeler C J, Zeltzer P M et al. Vaccination of malignant glioma patients with peptide-pulsed dendritic cells elicits systemic cytotoxicity and intracranial T-cell infiltration. *Cancer research* 61(3), 842-847 (2001).
85. Yamanaka R, Abe T, Yajima N et al. Vaccination of recurrent glioma patients with tumour lysate-pulsed dendritic cells elicits immune responses: results of a clinical phase I/II trial. *British journal of cancer* 89(7), 1172-1179 (2003).
86. Yu J S, Liu G, Ying H, Yong W H, Black K L, Wheeler C J. Vaccination with tumor lysate-pulsed dendritic cells elicits antigen-specific, cytotoxic T-cells in patients with malignant glioma. *Cancer research* 64(14), 4973-4979 (2004).
87. Yamanaka R, Honma J, Tsuchiya N, Yajima N, Kobayashi T, Tanaka R. Tumor lysate and IL-18 loaded dendritic cells elicits Th1 response, tumor-specific CD8+ cytotoxic T cells in patients with malignant glioma. *Journal of neuro-oncology* 72(2), 107-113 (2005).
88. Yamanaka R, Homma J, Yajima N et al. Clinical evaluation of dendritic cell vaccination for patients with recurrent glioma: results of a clinical phase I/II trial. *Clinical cancer research: an official journal of the American Association for Cancer Research* 11(11), 4160-4167 (2005).
89. Liau L M, Prins R M, Kiertscher S M et al. Dendritic cell vaccination in glioblastoma patients induces systemic and intracranial T-cell responses modulated by the local central nervous system tumor microenvironment. *Clinical cancer research: an official journal of the American Association for Cancer Research* 11(15), 5515-5525 (2005).
90. Walker D G, Laherty R, Tomlinson F H, Chuah T, Schmidt C. Results of a phase I dendritic cell vaccine trial for malignant astrocytoma: potential interaction with adjuvant chemotherapy. *Journal of clinical neuroscience: official journal of the Neurosurgical Society of Australasia* 15(2), 114-121 (2008).
91. Leplina O Y, Stupak V V, Kozlov Y P et al. Use of interferon-alpha-induced dendritic cells in the therapy of patients with malignant brain gliomas. *Bulletin of experimental biology and medicine* 143(4), 528-534 (2007).
92. De Vleeschouwer S, Fieuws S, Rutkowski S et al. Postoperative adjuvant dendritic cell-based immunotherapy in patients with relapsed glioblastoma multiforme. *Clinical cancer research: an official journal of the American Association for Cancer Research* 14(10), 3098-3104 (2008).
93. Ardon H, De Vleeschouwer S, Van Calenbergh F et al. Adjuvant dendritic cell-based tumour vaccination for children with malignant brain tumours. *Pediatric blood & cancer* 54(4), 519-525 (2010).
94. Prins R M, Soto H, Konkankit V et al. Gene expression profile correlates with T-cell infiltration and relative survival in glioblastoma patients vaccinated with dendritic cell immunotherapy. *Clinical cancer research: an official journal of the American Association for Cancer Research* 17(6), 1603-1615 (2011).
95. Okada H, Kalinski P, Ueda R et al. Induction of CD8+ T-cell responses against novel glioma-associated antigen peptides and clinical activity by vaccinations with {alpha}-type 1 polarized dendritic cells and polyinosinic-polycytidylic acid stabilized by lysine and carboxymethylcellulose in patients with recurrent malignant glioma. *Journal of clinical oncology: official journal of the American Society of Clinical Oncology* 29(3), 330-336 (2011).
96. Chang C N, Huang Y C, Yang D M et al. A phase I/II clinical trial investigating the adverse and therapeutic effects of a postoperative autologous dendritic cell tumor vaccine in patients with malignant glioma. *Journal of clinical neuroscience: official journal of the Neurosurgical Society of Australasia* 18(8), 1048-1054 (2011).
97. Iwami K, Shimato S, Ohno M et al. Peptide-pulsed dendritic cell vaccination targeting interleukin-13 receptor alpha2 chain in recurrent malignant glioma patients with HLA-A*24/A*02 allele. *Cytotherapy* 14(6), 733-742 (2012).
98. Fong B, Jin R, Wang X et al. Monitoring of regulatory T cell frequencies and expression of CTLA-4 on T cells, before and after DC vaccination, can predict survival in GBM patients. *PloS one* 7(4), e32614 (2012).
99. De Vleeschouwer S, Ardon H, Van Calenbergh F et al. Stratification according to HGG-IMMUNO RPA model predicts outcome in a large group of patients with relapsed malignant glioma treated by adjuvant postoperative dendritic cell vaccination. *Cancer immunology, immunotherapy: CII* 61(11), 2105-2112 (2012).
100. Phuphanich S, Wheeler C J, Rudnick J D et al. Phase I trial of a multi-epitope-pulsed dendritic cell vaccine for patients with newly diagnosed glioblastoma. *Cancer immunology, immunotherapy: CII* 62(1), 125-135 (2013).
101. Akiyama Y, Oshita C, Kume A et al. alpha-type-1 polarized dendritic cell-based vaccination in recurrent high-grade glioma: a phase I clinical trial. *BMC cancer* 12 623 (2012).
102. Prins R M, Wang X, Soto H et al. Comparison of glioma-associated antigen peptide-loaded versus autologous tumor lysate-loaded dendritic cell vaccination in malignant glioma patients. *Journal of immunotherapy* 36(2), 152-157 (2013).
103. Shah A H, Bregy A, Heros D O, Komotar R J, Goldberg J. Dendritic cell vaccine for recurrent high-grade gliomas in pediatric and adult subjects: clinical trial protocol. *Neurosurgery* 73(5), 863-867 (2013).
104. Reichardt V L, Okada C Y, Liso A et al. Idiotype vaccination using dendritic cells after autologous peripheral blood stem cell transplantation for multiple myeloma—a feasibility study. *Blood* 93(7), 2411-2419 (1999).
105. Lim S H, Bailey-Wood R. Idiotypic protein-pulsed dendritic cell vaccination in multiple myeloma. *International journal of cancer. Journal international du cancer* 83(2), 215-222 (1999).
106. Motta M R, Castellani S, Rizzi S et al. Generation of dendritic cells from CD14+ monocytes positively selected by immunomagnetic adsorption for multiple myeloma patients enrolled in a clinical trial of anti-idiotype vaccination. *British journal of haematology* 121(2), 240-250 (2003).
107. Reichardt V L, Milazzo C, Brugger W, Einsele H, Kanz L, Brossart P. Idiotype vaccination of multiple myeloma patients using monocyte-derived dendritic cells. *Haematologica* 88(10), 1139-1149 (2003).
108. Guardino A E, Rajapaksa R, Ong K H, Sheehan K, Levy R. Production of myeloid dendritic cells (DC) pulsed with tumor-specific idiotype protein for vaccination of patients with multiple myeloma. *Cytotherapy* 8(3), 277-289 (2006).
109. Lacy M Q, Mandrekar S, Dispenzieri A et al. Idiotype-pulsed antigen-presenting cells following autologous transplantation for multiple myeloma may be associated with prolonged survival. *American journal of hematology* 84(12), 799-802 (2009).
110. Yi Q, Szmania S, Freeman J et al. Optimizing dendritic cell-based immunotherapy in multiple myeloma: intranodal injections of idiotype-pulsed CD40 ligand-matured vaccines led to induction of type-1 and cytotoxic T-cell immune responses in patients. *British journal of haematology* 150(5), 554-564 (2010).
111. Rollig C, Schmidt C, Bornhauser M, Ehninger G, Schmitz M, Auffermann-Gretzinger S. Induction of cellular immune responses in patients with stage-I multiple myeloma after vaccination with autologous idiotype-pulsed dendritic cells. *Journal of immunotherapy* 34(1), 100-106 (2011).
112. Zahradova L, Mollova K, Ocadlikova D et al. Efficacy and safety of Id-protein-loaded dendritic cell vaccine in patients with multiple myeloma—phase II study results. *Neoplasma* 59(4), 440-449 (2012).
113. Timmerman J M, Czerwinski D K, Davis T A et al. Idiotype-pulsed dendritic cell vaccination for B-cell lymphoma: clinical and immune responses in 35 patients. *Blood* 99(5), 1517-1526 (2002).
114. Maier T, Tun-Kyi A, Tassis A et al. Vaccination of patients with cutaneous T-cell lymphoma using intranodal injection of autologous tumor-lysate-pulsed dendritic cells. *Blood* 102(7), 2338-2344 (2003).
115. Di Nicola M, Zappasodi R, Carlo-Stella C et al. Vaccination with autologous tumor-loaded dendritic cells induces clinical and immunologic responses in indolent B-cell lymphoma patients with relapsed and measurable disease: a pilot study. *Blood* 113(1), 18-27 (2009).
116. Hus I, Rolinski J, Tabarkiewicz J et al. Allogeneic dendritic cells pulsed with tumor lysates or apoptotic bodies as immunotherapy for patients with early-stage B-cell chronic lymphocytic leukemia. *Leukemia* 19(9), 1621-1627 (2005).
117. Li L, Giannopoulos K, Reinhardt P et al. Immunotherapy for patients with acute myeloid leukemia using autologous dendritic cells generated from leukemic blasts. *International journal of oncology* 28(4), 855-861 (2006).
118. Roddie H, Klammer M, Thomas C et al. Phase I/II study of vaccination with dendritic-like leukaemia cells for the immunotherapy of acute myeloid leukaemia. *British journal of haematology* 133(2), 152-157 (2006).
119. Litzow M R, Dietz A B, Bulur P A et al. Testing the safety of clinical-grade mature autologous myeloid DC in a phase I clinical immunotherapy trial of CML. *Cytotherapy* 8(3), 290-298 (2006).
120. Westermann J, Kopp J, Van Lessen A et al. Vaccination with autologous non-irradiated dendritic cells in patients with bcr/abl+ chronic myeloid leukaemia. *British journal of haematology* 137(4), 297-306 (2007).
121. Hus I, Schmitt M, Tabarkiewicz J et al. Vaccination of B-CLL patients with autologous dendritic cells can change the frequency of leukemia antigen-specific CD8+ T cells as well as CD4+CD25+FoxP3+ regulatory T cells toward an antileukemia response. *Leukemia* 22(5), 1007-1017 (2008).
122. Palma M, Adamson L, Hansson L et al. Development of a dendritic cell-based vaccine for chronic lymphocytic leukemia. *Cancer immunology, immunotherapy: CII* 57(11), 1705-1710 (2008).
123. Van Tendeloo V F, Van De Velde A, Van Driessche A et al. Induction of complete and molecular remissions in acute myeloid leukemia by Wilms' tumor 1 antigen-targeted dendritic cell vaccination. *Proceedings of the National Academy of Sciences of the United States of America* 107(31), 13824-13829 (2010).
124. Iwashita Y, Tahara K, Goto S et al. A phase I study of autologous dendritic cell-based immunotherapy for patients with unresectable primary liver cancer. *Cancer immunology, immunotherapy: CII* 52(3), 155-161 (2003).
125. Lee W C, Wang H C, Hung C F, Huang P F, Lia C R, Chen M F. Vaccination of advanced hepatocellular carcinoma patients with tumor lysate-pulsed dendritic cells: a clinical trial. *Journal of immunotherapy* 28(5), 496-504 (2005).
126. Butterfield L H, Ribas A, Dissette V B et al. A phase I/II trial testing immunization of hepatocellular carcinoma patients with dendritic cells pulsed with four alpha-fetoprotein peptides. *Clinical cancer research: an official journal of the American Association for Cancer Research* 12(9), 2817-2825 (2006).
127. Palmer D H, Midgley R S, Mirza N et al. A phase II study of adoptive immunotherapy using dendritic cells pulsed with tumor lysate in patients with hepatocellular carcinoma. *Hepatology* 49(1), 124-132 (2009).
128. El Ansary M, Mogawer S, Elhamid S A et al. Immunotherapy by autologous dendritic cell vaccine in patients with advanced HCC. *Journal of cancer research and clinical oncology* 139(1), 39-48 (2013).
129. Tada F, Abe M, Hirooka M et al. Phase I/II study of immunotherapy using tumor antigen-pulsed dendritic cells in patients with hepatocellular carcinoma. *International journal of oncology* 41(5), 1601-1609 (2012).
130. Ueda Y, Itoh T, Nukaya I et al. Dendritic cell-based immunotherapy of cancer with carcinoembryonic antigen-derived, HLA-A24-restricted CTL epitope: Clinical outcomes of 18 patients with metastatic gastrointestinal or lung adenocarcinomas. *International journal of oncology* 24(4), 909-917 (2004).
131. Hirschowitz E A, Foody T, Kryscio R, Dickson L, Sturgill J, Yannelli J.
Autologous dendritic cell vaccines for non-small-cell lung cancer. *Journal of clinical oncology: official journal of the American Society of Clinical Oncology* 22(14), 2808-2815 (2004).
132. Chang G C, Lan H C, Juang S H et al. A pilot clinical trial of vaccination with dendritic cells pulsed with autologous tumor cells derived from malignant pleural effusion in patients with late-stage lung carcinoma. *Cancer* 103(4), 763-771 (2005).
133. Yannelli J R, Sturgill J, Foody T, Hirschowitz E. The large scale generation of dendritic cells for the immunization of patients with non-small cell lung cancer (NSCLC). *Lung cancer* 47(3), 337-350 (2005).
134. Ishikawa A, Motohashi S, Ishikawa E et al. A phase I study of alpha-galactosylceramide (KRN7000)-pulsed dendritic cells in patients with advanced and recurrent non-small cell lung cancer. *Clinical cancer research: an official journal of the American Association for Cancer Research* 11(5), 1910-1917 (2005).

135. Antonia S J, Mirza N, Fricke I et al. Combination of p53 cancer vaccine with chemotherapy in patients with extensive stage small cell lung cancer. *Clinical cancer research: an official journal of the American Association for Cancer Research* 12(3 Pt 1), 878-887 (2006).

136. Perrot I, Blanchard D, Freymond N et al. Dendritic cells infiltrating human non-small cell lung cancer are blocked at immature stage. *Journal of immunology* 178(5), 2763-2769 (2007).

137. Hirschowitz E A, Foody T, Hidalgo G E, Yannelli J R. Immunization of NSCLC patients with antigen-pulsed immature autologous dendritic cells. *Lung cancer* 57(3), 365-372 (2007).

138. Baratelli F, Takedatsu H, Hazra S et al. Pre-clinical characterization of GMP grade CCL21-gene modified dendritic cells for application in a phase I trial in non-small cell lung cancer. *Journal of translational medicine* 6 38 (2008).

139. Hegmans J P, Veltman J D, Lambers M E et al. Consolidative dendritic cell-based immunotherapy elicits cytotoxicity against malignant mesothelioma. *American journal of respiratory and critical care medicine* 181(12), 1383-1390 (2010).

140. Um S J, Choi Y J, Shin H J et al. Phase I study of autologous dendritic cell tumor vaccine in patients with non-small cell lung cancer. *Lung cancer* 70(2), 188-194 (2010).

141. Chiappori A A, Soliman H, Janssen W E, Antonia S J, Gabrilovich D I. INGN-225: a dendritic cell-based p53 vaccine (Ad.p53-D C) in small cell lung cancer: observed association between immune response and enhanced chemotherapy effect. *Expert opinion on biological therapy* 10(6), 983-991 (2010).

142. Perroud M W, Jr., Honma H N, Barbeiro A S et al. Mature autologous dendritic cell vaccines in advanced non-small cell lung cancer: a phase I pilot study. *Journal of experimental & clinical cancer research: CR* 30 65 (2011).

143. Skachkova O V, Khranovska N M, Gorbach O I, Svergun N M, Sydor R I, Nikulina V V. Immunological markers of anti-tumor dendritic cells vaccine efficiency in patients with non-small cell lung cancer. *Experimental oncology* 35(2), 109-113 (2013).

144. Hernando J J, Park T W, Kubler K, Offergeld R, Schlebusch H, Bauknecht T. Vaccination with autologous tumour antigen-pulsed dendritic cells in advanced gynaecological malignancies: clinical and immunological evaluation of a phase I trial. *Cancer immunology, immunotherapy: CII* 51(1), 45-52 (2002).

145. Rahma O E, Ashtar E, Czystowska M et al. A gynecologic oncology group phase II trial of two p53 peptide vaccine approaches: subcutaneous injection and intravenous pulsed dendritic cells in high recurrence risk ovarian cancer patients. *Cancer immunology, immunotherapy: CII* 61(3), 373-384 (2012).

146. Chu C S, Boyer J, Schullery D S et al. Phase I/II randomized trial of dendritic cell vaccination with or without cyclophosphamide for consolidation therapy of advanced ovarian cancer in first or second remission. *Cancer immunology, immunotherapy: CII* 61(5), 629-641 (2012).

147. Kandalaft L E, Chiang C L, Tanyi J et al. A Phase I vaccine trial using dendritic cells pulsed with autologous oxidized lysate for recurrent ovarian cancer. *Journal of translational medicine* 11 149 (2013).

148. Lepisto A J, Moser A J, Zeh H et al. A phase I/II study of a MUC1 peptide pulsed autologous dendritic cell vaccine as adjuvant therapy in patients with resected pancreatic and biliary tumors. *Cancer therapy* 6(B), 955-964 (2008).

149. Rong Y, Qin X, Jin D et al. A phase I pilot trial of MUC1-peptide-pulsed dendritic cells in the treatment of advanced pancreatic cancer. *Clinical and experimental medicine* 12(3), 173-180 (2012).

150. Endo H, Saito T, Kenjo A et al. Phase I trial of preoperative intratumoral injection of immature dendritic cells and OK-432 for resectable pancreatic cancer patients. *Journal of hepato-biliary-pancreatic sciences* 19(4), 465-475 (2012).

151. Lawrence H S, Pappenheimer A M, Jr. Transfer of delayed hypersensitivity to diphtheria toxin in man. *The Journal of experimental medicine* 104(3), 321-335 (1956).

152. Rosenfeld S, Dressler D. Transfer factor: a subcellular component that transmits information for specific immune responses. *Proceedings of the National Academy of Sciences of the United States of America* 71(6), 2473-2477 (1974).

153. Dressler D, Rosenfeld S. On the chemical nature of transfer factor. *Proceedings of the National Academy of Sciences of the United States of America* 71(11), 4429-4434 (1974).

154. Shifrine M, Scibienski R. Transfer factor—hypotheses for its structure and function. *Oncology* 32(5-6), 269-274 (1975).

155. Kirkpatrick C H. Properties and activities of transfer factor. *The Journal of allergy and clinical immunology* 55(6), 411-421 (1975).

156. Burger D R, Vandenbark A A, Daves D, Anderson W A, Jr., Vetto R M, Finke P. Human transfer factor: fractionation and biologic activity. *Journal of immunology* 117(3), 789-796 (1976).

157. Berron-Perez R, Chavez-Sanchez R, Estrada-Garcia I et al. Indications, usage, and dosage of the transfer factor. *Revista alergia Mexico* 54(4), 134-139 (2007).

158. Kirkpatrick C H. Restoration of cell-mediated immune responses with transfer factor. *Birth defects original article series* 11(1), 441-444 (1975).

159. Rocklin R E. Use of transfer factor in patients with depressed cellular immunity and chronic infection. *Birth defects original article series* 11(1), 431-435 (1975).

160. Grob P J. Therapeutic use of transfer factor. *European journal of clinical investigation* 5(1), 33-43 (1975).

161. Pizza G, Meduri R, De Vinci C, Scorolli L, Viza D. Transfer factor prevents relapses in herpes keratitis patients: a pilot study. *Biotherapy* 8(1), 63-68 (1994).

162. Estrada-Parra S, Chavez-Sanchez R, Ondarza-Aguilera R et al. Immunotherapy with transfer factor of recurrent herpes simplex type I. *Archives of medical research* 26 Spec No S87-92 (1995).

163. Meduri R, Campos E, Scorolli L, De Vinci C, Pizza G, Viza D. Efficacy of transfer factor in treating patients with recurrent ocular herpes infections. *Biotherapy* 9(1-3), 61-66 (1996).

164. Estrada-Parra S, Nagaya A, Serrano E et al. Comparative study of transfer factor and acyclovir in the treatment of herpes zoster. *International journal of immunopharmacology* 20(10), 521-535 (1998).

165. Neidhart J A, Lobuglio A F. Transfer factor: Potential for therapy of malignant diseases. *Archives of otolaryngology* 101(11), 664-666 (1975).
166. Levin A S, Byers V S, Fudenberg H H et al. *Osteogenic sarcoma*. Immunologic parameters before and during immunotherapy with tumor-specific transfer factor. *The Journal of clinical investigation* 55(3), 487-499 (1975).
167. Ng R P, Moran C J, Alexopoulos C G, Bellingham A J. Transfer factor in Hodgkin's disease. *Lancet* 2(7941), 901-903 (1975).
168. Vetto R M, Burger D R. Transference of cell mediated immunity in patients with head and neck cancer. *The Laryngoscope* 88(1 Pt 2 Suppl 8), 79-82 (1978).
169. Krown S E, Pinsky C M, Hirshaut Y, Hansen J A, Oettgen H F. Effects of transfer factor in patients with advanced cancer. *Israel journal of medical sciences* 14(10), 1026-1038 (1978).
170. Wagner G, Knapp W, Gitsch E, Selander S. Transfer factor for adjuvant immunotherapy in cervical cancer. *Cancer detection and prevention. Supplement: official publication of the International Society for Preventive Oncology, Inc* 1 373-376 (1987).
171. Whyte R I, Schork M A, Sloan H, Orringer M B, Kirsh M M. Adjuvant treatment using transfer factor for bronchogenic carcinoma: long-term follow-up. *The Annals of thoracic surgery* 53(3), 391-396 (1992).
172. Dupont B, Ballow M, Hansen J A, Quick C, Yunis E J, Good R A. Effect of transfer factor therapy on mixed lymphocyte culture reactivity. *Proceedings of the National Academy of Sciences of the United States of America* 71(3), 867-871 (1974).
173. Ballow M, Dupont B, Hansen J A, Good R A. Transfer factor therapy: evidence for nonspecificity. *Birth defects original article series* 11(1), 457-461 (1975).

The invention claimed is:

1. A method of immune modulation wherein a host is suffering from a tumor, comprising: a) providing an immunogenic dendritic cell, wherein said dendritic cell is in an immature state; b) preparing said immunogenic cell to allow for uptake of mRNA; c) contacting mRNA that encodes for a survivin peptide with said immunogenic dendritic cell in a manner allowing for the immature dendritic cell to uptake said mRNA and then transcribe of said mRNA; and d) contacting a damage-associated molecular pattern (DAMP) or other maturation signal to said immature dendritic cell in an amount sufficient to mature said dendritic cell; and e) administering said mature immunogenic dendritic cell to the host in need of immune modulation, in an amount sufficient to treat said tumor.

2. The method of claim 1, wherein said survivin peptide is selected from the group consisting of:

a)
STFKNWPFL; (SEQ ID NO: 1)

b)
STFKNWPFMRYMILGLLAL; (SEQ ID NO: 2)

c)
TTALSSTFKNWPFL; (SEQ ID NO: 3)
and d)
MASTFKNWPFAAAAAG. (SEQ ID NO: 4)

3. The method of claim 1, wherein said mRNA comprises a 3' tailing sequence of linked nucleosides of approximately 140 nucleotides.

4. The method of claim 3, wherein said mRNA comprises a 5' terminal cap of Cap1.

5. The method of claim 1, wherein said mRNA comprises at least one chemically modified nucleoside.

6. The method of claim 5, wherein the at least one chemically modified nucleoside is selected from the group consisting of: pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methylpseudouridine, 4-thio-1-methylpseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-i sopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methyl-guanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

7. The method of claim 1, wherein said mRNA is formulated.

8. The method of claim 7, wherein the mRNA formulation is a lipoplex formulation.

9. The method of claim 7, wherein the mRNA formulation comprises a lipid selected from the group consisting of: DLin-DMA, DLin-K-DMA, DLin-KC2-DMA, 98N12-5, C12-200, DLin-MC 3-DMA, DODMA, DSDMA, DLenDMA, reLNPs, PLGA, and PEGylated lipids.

10. The method of claim 1, wherein the DAMP or maturation signal is contacted with the immature dendritic cell ex vivo.

11. The method of claim 1, wherein the DAMP or maturation signal is contacted with the immature dendritic cell in vivo.

12. The method of claim 1, wherein the survivin protein is STFKNWPFMRYMILGLLAL (SEQ ID NO: 2).

13. The method of claim 5, wherein the modified nucleoside is pyridine-4-one ribonucleoside.

* * * * *